United States Patent [19]

Fujise

[11] Patent Number: 4,641,328
[45] Date of Patent: Feb. 3, 1987

[54] COMPUTED TOMOGRAPHY APPARATUS

[75] Inventor: Masakuni Fujise, Nishinasuno, Japan

[73] Assignee: Tokyo Shibaura Denki Kabushiki Kaisha, Japan

[21] Appl. No.: 515,904

[22] Filed: Jul. 21, 1983

[30] Foreign Application Priority Data

Jul. 21, 1982 [JP] Japan ................. 57-125906

[51] Int. Cl.⁴ ......................... H05G 1/10; H05G 1/64; A61B 6/00
[52] U.S. Cl. ......................................... 378/8; 378/95; 378/99; 358/111
[58] Field of Search ....................... 378/8, 98, 99, 100, 378/901, 95; 364/414

[56] References Cited

U.S. PATENT DOCUMENTS

| | | | |
|---|---|---|---|
| 3,952,201 | 4/1976 | Hounsfield | 378/8 |
| 4,035,647 | 7/1977 | Hounsfield et al. | |
| 4,047,044 | 9/1977 | Weaver | 378/98 |
| 4,075,492 | 2/1978 | Boyd et al. | |
| 4,149,247 | 4/1979 | Pavkovich et al. | |
| 4,178,511 | 12/1979 | Hounsfield et al. | 378/901 |
| 4,182,311 | 2/1980 | Seppi et al. | |
| 4,467,352 | 8/1984 | Saalfrank | 378/99 |

FOREIGN PATENT DOCUMENTS 1949899 4/1971 Fed. Rep. of Germany .
2257772 5/1974 Fed. Rep. of Germany ........ 378/99
0140492 10/1979 Japan ..................................... 378/99

OTHER PUBLICATIONS

Farmer et al, "Cine-CT Captures the Beating Heart", Diagnostic Imaging, Oct. 1984.
Fleisch, "The VP 450 Data System–A New Evaluation System for Use with Gamma Cameras", Electromedia, Germany, No. 2 (1978).

Primary Examiner—Craig E. Church
Assistant Examiner—Charles F. Wieland
Attorney, Agent, or Firm—Finnegan, Henderson, Farabow, Garrett & Dunner

[57] ABSTRACT

Computed tomography apparatus in which data is acquired during one or more full rotational cycles and suitably stored by scanning a beating heart or similar objects and in which a complete image corresponding to a cross section of the beating heart is produced on a CRT screen and is correlated with a specific portion of the heart cycle reconstructed from the limited data taken during a time interval which is a small fraction of the duration of the heart cycle. Advantageously, the apparatus presents the cross section image of the beating heart and reference data correlated with certain parameters of the cross-section display on the same CRT screen.

5 Claims, 2 Drawing Figures

COMPUTED TOMOGRAPHY APPARATUS

BACKGROUND OF THE INVENTION

This invention is related to apparatus for examining an object by means of radiation such as x- or gamma-radiation. More particularly, the invention is concerned with computed tomographic apparatus which provides a complete image corresponding to a cross-section of the beating heart produced on a cathode-ray tube display during a time interval which is a small fraction of the duration of the heart cycle and which corresponds to a specific portion of the heart cycle.

Computerized tomography permits the production of a representation of the variation, over a cross-sectional slice of a body under examination, of the absorption or transmission coefficient with respect to the penetrating radiation, such as X-radiation. Such representations provide a considerable amount of clinically useful information and, in particular, enable tumors or tissue damage to be identified and accurately located without the need for surgery or invasive diagnostic procedures.

Various techniques for performing computerized tomography are described in U.S. Pat. No. 4,035,647 and in U.S. Pat. No. 4,075,492 and other techniques are disclosed in U.S. Pat. No. 4,149,247. The former techniques offer potentially rapid data acquisition employing a fan-shaped beam, and the latter techniques are concerned primarily with the reconstruction method for a fan beam source which employs a convolution method of data reconstruction, without the prior reordering of fan rays, to eliminate errors in the measurements and delay in computation time which would otherwise be involved in such reordering. Rapid data acquisition and fast reconstruction are important because if the data is acquired rapidly, and the tomograph is reconstructed quickly based upon the data acquired, there is less chance of the representation being marred by artifacts due to movement of the body under examination, or of organs or fluids therein, during the acquisition time.

In principle, with the technique described in U.S. Pat. No. 4,035,647 the radiation is constrained to conform to a fan-shaped spread, emanating from a small source area, and the radiation is projected through the body. The fan angle of the spread of radiation is sufficient to embrace at least a substantial part of the slice of the body and the source is rotated around the body about an axis intersecting the slice. The array of detector devices is provided to receive radiation projected through the body and to provide output signals which are sampled at a rapid rate. The individual output signals are attributable to respective beam paths traversed by the radiation through the body.

In recent years it has been proposed to apply computed tomography apparatus to examination of organs of a body in a relatively stationary condition. Such a method and system are described in U.S. Pat. No. 4,182,311 issued to Edward J. Seppi et al.

Raw projection data is collected during one or more continuous cycles of rotation while scanning, the acquired data is stored for use in the reconstruction process and is identified positively with portions of the organ cycle, and the desired cross-sectional image is reconstructed by correlating the stored data with the portion or phase of the cyclic movement of the body organ under examination.

The above apparatus has several disadvantages. In the conventional apparatus, only the projections are processed to reconstruct the image on the display device corresponding to a selected cardiac phase. However, unlike the present invention a series of reference electrocardiogram signals are not indicated on the same display device screen to show information correlated with the reconstructed image. Hence, it is impossible to simultaneously view the described cross-sectional image during the selected cardiac phase with the reference electrocardiogram information.

Furthermore there is no teaching nor suggestion of how the display device makes the information visible simultaneously on the same screen for convenient and comparative observation by an operator.

SUMMARY OF THE INVENTION

An object of the present invention is to provide novel and improved computed tomography techniques and apparatus for producing and displaying on a single cathode ray tube screen a cross-section of the beating heart, during a time interval corresponding to a selected cardiac phase in a cardiac cycle, together with correlated electrocard iogram information.

Another object is to display indicators or cursors on the same cathode-ray tube screen which represent the specific cardiac phase in the heart cycle at which the displayed cross-sectional image of the beating heart was taken.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention as embodied and broadly described herein, the computed tomography apparatus of the invention comprises means for directing a divergent beam of penetrating radiation through a body to be examined; means for effecting relative angular displacement between the divergent beam of penetrating radiation and the body irrespective of the cardiac cycle of the body; means for detecting the penetrating radiation that passes through the body at a number of angular positions of the divergent beam relative to the body during said relative angular displacement to derive sets of detected radiation measurements representative of attenuation of the penetrating radiation by the body; display means including a cathode ray tube having a display screen; ECG detector means for generating electrocardiogram signals, during said relative angular displacement, corresponding to electrical signals of the heart created during each cardiac cycle; means for storing the radiation measurements detected by said detecting means together with data corresponding to the electrocardiogram signals generated from said ECG detector means, said electrocardiogram data being associated with said radiation measurements when such data is acquired in that said radiation measurements are correlated with the various cardiac phases of the cardiac cycles represented in such data; sequence control means for selecting specific phases of the cardiac cycle during which cross-sectional images of the examined body will be reconstructed and displayed; means for reconstructing the cross-sectional images of the body corresponding to the selected cardiac phases and said detected radiation measurements associated therewith and including display interface means for providing video signals corresponding to said cross-sectional images on said display screen of the cathode ray tube; and means for providing on said display screen an electrocardiogram display corresponding to the electrocardiogram data in said storing means upon the selection of a specific cardiac phase by said sequence control means.

The accompanying drawings, which are incorporated in and constitute a part of this specification, illustrate one embodiment of the invention and, together with the description, serve to explain the principles of the invention.

DESCRIPTION OF THE PREFERRED EMBODIMENT

Figure 1:
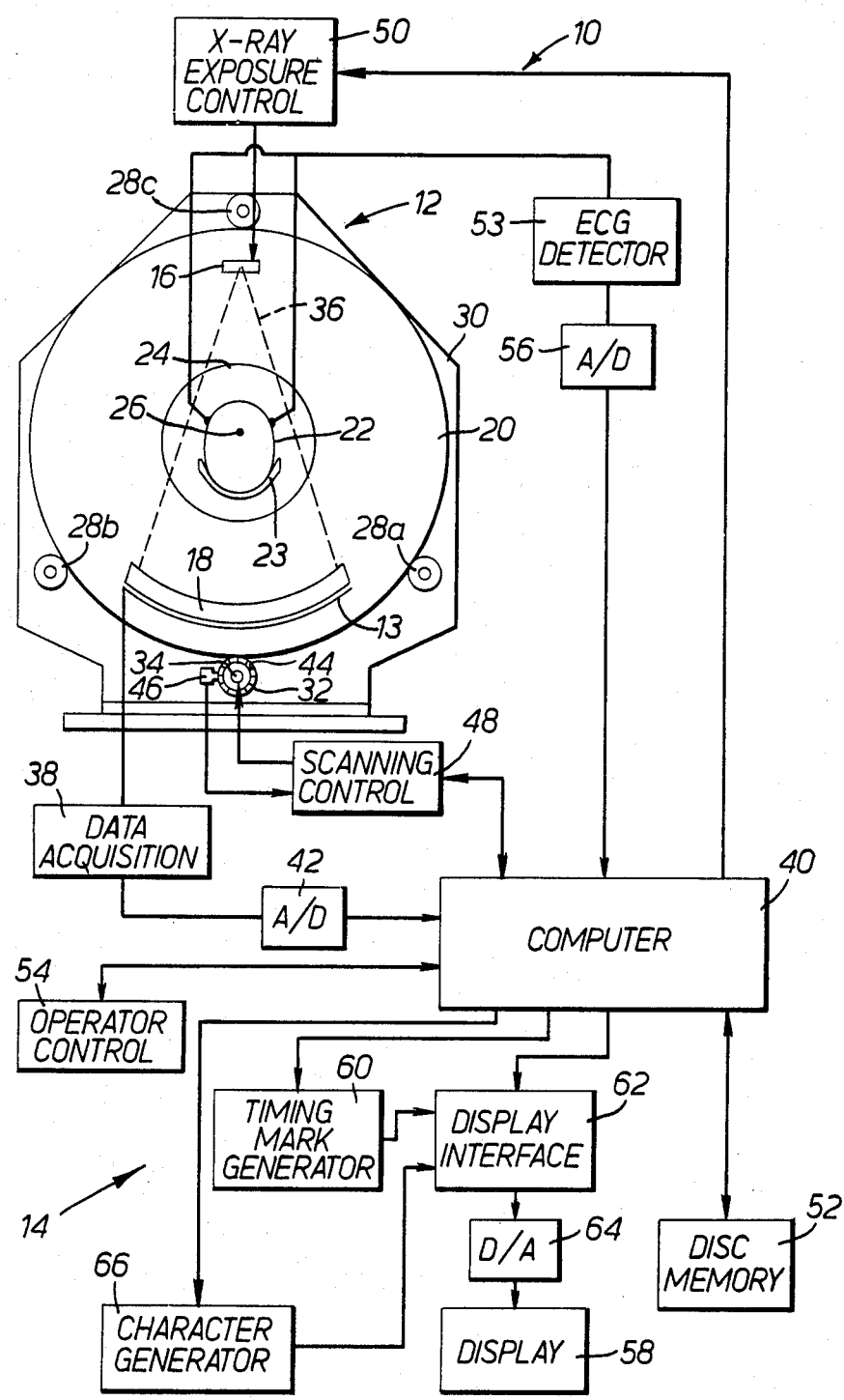
FIG. 1 shows in block form a schematic arrangement of the preferred embodiment of the invention.

Referring now to the drawings, particularly FIG. 1, there is shown a computerized tomography apparatus 10 embodying the present invention. Apparatus 10 comprises a computerized tomography scanner assembly 12 and processing electronics 14. Computerized tomography scanner assembly 12 includes an X-ray source 16, an array of detector devices 18 and a rotatable assembly 20. The body 22 supported on the bed 23 is inserted into an opening 24 in the rotatable assembly 20 so that a selected cross-sectional slice of the body 22 is disposed in the opening 24. The rotatable member 20 is arranged to rotate about an axis 26, longitudinal of the body 22 and perpendicular to the paper. For that purpose, for example, the rotatable member 20 is supported and guided by three gear wheels 28a, 28b, 28c which engage with gear teeth (not shown) cut into the periphery of member 20. The gear wheels 28 are journalled in a main frame 30 of the apparatus, which may take any form suitable to support the apparatus and to allow the necessary rotation. A further cog wheel 32, also engaging with the gear teeth is driven by an electric motor 34, also mounted on the main frame 30 and serves to provide the required rotary motion.

The rotatable member 20 also carries the X-ray source 16 and the array of detector devices 18. The detectors can be of any suitable type, for example scintillation crystals with associated photomultipliers or photodiodes. With a collimator, not shown, the X-ray beam emanating from the X-ray source 16 is shaped into a thin fan-shaped beam whose boundaries are indicated by the diverging dashed lines 36. The X-ray source 16 and the array of detector devices 18 are mounted to rotate together about axis 26 and body 22. The X-ray source 16 is pulsed on and off at regular intervals during rotational movement and each cell in the array of detector devices 18 produces an analog signal representative of absorption of the X-radiation by each small volume element arranged in series along ray paths extending from the X-ray source 16 to the cells. The absorption data for each incremental angle of rotation by the X-ray source 16 and the array of detector devices is acquired in data acquisition apparatus 38 which is elementary to CT apparatus and need not be described.

The absorption data for a complete scan of the body 22 is inputted to a computer (CPU) 40, via an analog-to-digital converter 42 for converting the absorption data into corresponding digital signals. The computer 40 is controlled by a suitable algorithm to process the data in a manner to display a reconstructed image of the layer of the body which has been scanned by the fan-shaped X-ray beam. To provide the information regarding the rotation, a circular graticule 44 is mounted coaxially on the shaft of the cog wheel 32. This circular graticule 44 takes the form of a translucent ring carrying radial engraved lines. The lines can interrupt a light path between a light source and photocell included in a photocell unit 46 mounted on the main frame 30. Thus as the cog wheel 32 rotates, driving the rotatable assembly 20, successive lines interrupt the light path and the photocell unit 46 provides pulses indicative of the angular position of the rotatable member 20 and, thus, the X-ray source 16 and the array of detector devices 18 relative to the body 22. In other words, the radial or angular position of the body is correlated with the projection data. The pulse signal, representative of the position of the rotatable assembly 20, is fed to a scanning control 48 for setting and resetting at the desired intervals thus providing the signals to the computer 40 which operates on the signals to evaluate the absorption coefficient at each of a plurality of locations distributed over the examined region of the body 22. The output of the scanning control 48 is fed to the motor 34 for driving the rotatable assembly 20 continously around the body 22 through more than 180 degrees. The X-ray source 16 is of conventional design, but is equipped with a X-ray exposure control 50 which controls the pulsing of the X-ray source 16 in response to command signals initiated from computer 40.

The data for displaying reconstructed images of one or more body layers which has been temporarily stored in the memory of computer 40 can be transferred to disc memory 52. For correlating the slice of interest, i.e., the slice associated with a particular point in time in the cardiac cycle, with the projection pertinent thereto, an electrocardiogram unit is coupled to the patient, which comprises an electrocardiogram (ECG) detector 53, shown connected to electrodes on the arms of the patient's body and to an electrode positioned on the chest adjacent the heart. Additional electrodes (not shown) are connected to the ECG detector 53 and may be positioned on the patient legs or at other points of the body 22.

The ECG detector 53 functions to produce a signal having a waveform corresponding to electrical signals at the heart, which signal is applied to an analog-to-digital converter 56 operative to digitize the electrocardiogram signals. The digitized data is transferred to the disc memory 52 via computer 40 for storage in a predetermined sequence (which will be explained in detail below).

Computer 40 generates control signals for the entire system in response to command signals initiated from an operator console 54. Individual absorption data detected by the array of detector devices 18, the projection angles at which data was acquired and the cardiac phase signals provided at a repetition rate indicative of a predetermined fraction of one complete cardiac cycle are transferred to the disc memory 52 via computer 40. The disc memory 52 is operative to complement the computer memory and to store data and programs for controlling system operation. In response to command signals generated from the operator console 54, the stored data is read from the disc memory 52 and applied to a display 58 via computer 40 for data presentation.

An operator enters the desired operation into computer 40 via a keyboard (not shown) on the operator console 54. During operation the computer 40 receives several different signals for the display 58 and from the operator console 54. The first is a signal informing the computer 40 that the X-ray exposure control 50, the scanning control 48, the data acquisition 38 and the ECG detector 53 have been activated. The assembly 20 rotates continuously in a clockwise direction, and for each predetermined incremental angle, such as 0.6 degrees, the array of detector devices 18 provides output signals indicative of the beam paths through the body. The computer 40 must know the number of divisions of the cardiac cycle and the cardiac phase of interest (shown by the position of a cursor relative to the electrocardiogram waveform). In addition the apparatus includes a timing mark generator 60 which operates to insert an unblanking signal corresponding to the selected cardiac phase into the composite video signal based upon the data read out from the disc memory 52 at a display data memory (not shown) of the display data interface 62.

Thus, the display will present the cursor 76 (FIG. 2) at the position on the electrocardiogram waveform corresponding to the selected cardiac phase, as described later herein.

The summed digital composite signals are converted into the analog composite video signals in an analog-to-digital converter 64. The analog output of the digital-to-analog converter 64 is supplied to the display 58. Thus, for example, the particular portion of the electrocardiogram waveform corresponding to the selected cardiac phase may be unblanked to produce the cursor superimposed on the electrocardiogram waveform on the display screen. The character code data in the computer 40 is applied to a character generator 66. The character generator 66 may be any of the well known types of read only memories (ROM) which provide appropriate output signals in response to the code information designating particular characters as supplied by the computer 40. The output of the character generator 66 is summed at the display data interface 62 to become part of the composite digital signal to the display 56. The disc memory 52 is programmed so that each absorption data for each increment of rotation by the X-ray source 16 and the array of detector devices 18 is stored with data indicating the correlation of the rotatable assembly angular position with the cardiac phase [incorporating digital data responsive to the amplitude of the signals received by the ECG detector 53].

Figure 2:
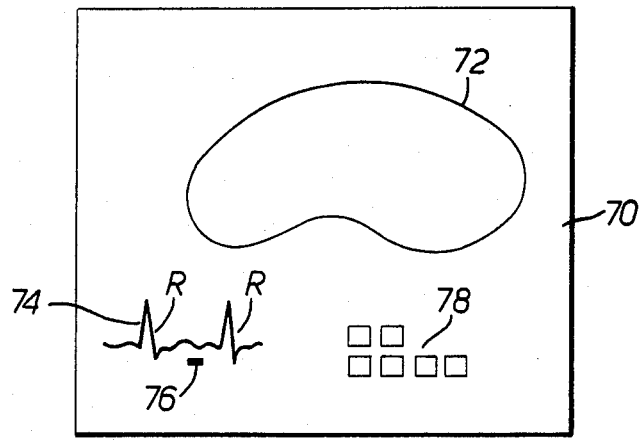
FIG. 2 depicts a view of the cathode-ray tube screen for illustrating schematically the display achieved by the present invention.

Reference is now made to FIG. 2 which illustrates a typical visual presentation which might be presented in accordance with the present invention. The screen 70 of the display 56 displays the desired cross-sectional image during the selected cardiac phase as indicated by number 72, and includes ECG waveform indicated by number 74. Directly below the ECG waveform 74 there is the cursor 76 comprised of several vertical sweeps, and at the right is digital character display 78 which identifies the phase of the cardiac cycle corresponding to the position of the cursor 76 relative to a spike at time R representing the electrical activity of the heart muscles associated with the contraction of the ventricle.

The entire function of the apparatus is controlled by a suitable computer program through a conventional programmable digital computer. When the subject is suitably positioned in the apparatus, as shown in FIG. 1, the motor 34 is energized starting rotation of rotating assembly 20 by the scanning control 48. High voltage power is supplied to the X-ray source 16. The X-ray source 16 is pulsed for very short durations such as 600 times in the course of one complete 360 rotation. Normally one rotation will be completed in five seconds or less. At the end of one complete rotation, the rotating assembly 20 stops during the time between scans required to cool the X-ray equipment, and a new scan is started. Depending on the power used in the X-ray beam and the above mentioned cooling time, as many as three or more discrete full power scans of 360 degrees each can be completed in one minute.

Since the array of detector devices 18 takes measurements for each pulse and the X-ray source 16 is pulsed from 600 separate positions during one 360 degree rotation of the assembly, there are about 300,000 total measurements taken in each 360 degree rotation of the rotating assembly 20 assuming 500 detectors devices 18. The value measured is the attenuation of the X-ray beam which passes into the array of detector devices 18. These attenuation measurements are read through the data acquisition device 38 and digitized by the analog-to-digital converter 42. The digitized value is stored in the computer 40 or the disc memory 52.

The disc memory 52 is actuated by controls on the operator control 54 via computer 40. The operator control 54 generates an electrocardiogram data transfer request via the computer 40 to the disc memory 52. At this point, the electrocardiogram data representing at least one complete cardiac cycle in the disc memory 52 is read out and fed into the memory of the display data interface 62. This digital electrocardiogram data read from the disc memory is converted into the analog video signal by the digital-to-analog converter 64 and then supplied to the display 56 which presents the electrocardiogram waveform 74. Concurrently, the total measurements for each scan are read out and transferred into the computer 40, in which the absorption data is convolved and appropriately stored and later back-projected to provide a conventional cross-sectional image 72 of the body 22 under examination via the display data interface 62 and the digital-to-analog converter 64 on the display screen 70. Next, the operator control 54 generates a data transfer request signal to the disc memory 52 via computer 40 in accordance with the particular phase of the cardiac phase selected by the operator. The absorption data stored in the disc memory 52 corresponding to the selected cardiac phase is read out of the disc memory 52 and collected in the memory of computer 40 to reconstruct the cross-sectional image of the body corresponding to the particular phase of the cardiac cycle by performing the above processing on these data in the same manner. The signal representing the selected cardiac phase generated from the operator control 54 is also supplied to the timing mark generator 60. The timing mark generator 60 generates a digital signal for presenting the cursor 76 at the predetermined position on the display screen 70 to the display data interface 62. The desired point in the cardiac cycle is selected from the operator control 54 and the value representing the position of the selected cardiac phase relative to the spike at R (FIG. 2), representing the electrical activity of the heart muscles associated with the contraction of the ventricle, are supplied to the charactor generator 66 which provides the appropriate digital output. The output is converted to the binary coded decimal available for display.

It will be apparent to those skilled in the art that for the purpose of providing fully acceptable images in terms of blurring, density and resolution, the absorption data corresponding to the adjacent cardiac phase is also utilized for reconstructing the desired cross-sectional image of the body with the data corresponding to the selected cardiac phase in response to the command initiated from computer 40.

While the description above specifically illustrates the embodiment employing an ECG detector, it should be apparent that the apparatus according to the present invention can employ a phonocardiogram detector, and provide a cross-sectional image of the body corresponding to a particular point in time in a pulsation.

While the present invention has been described with reference to particular embodiments thereof, it will be understood by those skilled in the art that numerous modifications can be made without actually departing from the scope of the invention. Accordingly, all modifications and equivalents may be resorted to which fall within the scope of the invention as claimed.

What is claimed is:

1. A computed tomography apparatus for reconstructing cross-sectional images of a body to be examined corresponding to selected cardiac phases of the cardiac cycle, comprising:
   means for directing a divergent beam of penetrating radiation through the body;
   means for effecting relative angular displacement between the divergent beam of penetrating radiation and the body irrespective of the cardiac cycle of the body;
   means for detecting the penetrating radiation that passes through the body at a number of angular positions of the divergent beam relative to the body during said relative angular displacement to derive sets of detected radiation measurements representative of attenuation of the penetrating radiation by the body;
   display means including a cathode ray tube having a display screen;
   ECG detector means for generating electrocardiogram signals, during said relative angular displacement, corresponding to electrical signals of the heart created during each cardiac cycle;
   means for storing the radiation measurements detected by said detecting means, together with data corresponding to the electrocardiogram signals generated from said ECG detector means said electrocardiogram data being associated with said radiation measurements when such data is acquired in that said radiation measurements are correlated with the various cardiac phases of the cardiac cycles represented in such data;
   sequence control means for selecting specific phases of the cardiac cycle during which cross-sectional images of the examined body will be reconstructed and displayed;
   means for reconstructing the cross-sectional images of the body corresponding to the selected cardiac phases and said detected radiation measurements associated therewith and including display interface means for providing video signals corresponding to said cross-sectional images on said display screen of the cathode ray tube; and
   means for providing on said display screen an electrocardiogram display corresponding to the stored electrocardiogram data in said storing means upon the selection of a specific cardiac phase by said sequence control means.

2. The computed tomography apparatus of claim 1, wherein:
   said electrocardiogram display providing means is operative to provide a cursor display indicating said selected cardiac phase relative to said electrocardiogram display on said screen of the cathode ray tube.

3. The computed tomography apparatus of claim 2, further comprising:
   a timing mark generator for producing video signals for said cursor display.

4. The computer tomography apparatus of claim 3, wherein:
   said display interface means includes a video mixing circuit for mixing the video signals corresponding to said cross-sectional images, video signals corresponding to said cursors, and video signals corresponding to said electrocardiogram display, and providing composite video siganls for said display screen.

5. The computed tomography apparatus of claim 4, further comprising:
   a character signal generating means coupled to said sequence control means and responsive thereto for generating signals for producing on said display screen a digital character display.

* * * * *